United States Patent [19]

Gibbs

[11] Patent Number: 5,773,454

[45] Date of Patent: Jun. 30, 1998

[54] BENZOFUROXAN DERIVATIVES FOR USE AS INSECT FEEDING DETERRENTS

[75] Inventor: Don E. Gibbs, Kansas City, Mo.

[73] Assignee: Rockhurst University, Kansas City, Mo.

[21] Appl. No.: 820,838

[22] Filed: Mar. 20, 1997

Related U.S. Application Data

[60] Provisional application No. 60/013,817 Mar. 21, 1996.

[51] Int. Cl.[6] ........................................... A01N 43/82
[52] U.S. Cl. ....................... 514/364; 424/DIG. 10; 514/919
[58] Field of Search ..................... 514/364, 919; 424/DIG. 10

[56] References Cited

U.S. PATENT DOCUMENTS

| | | | |
|---|---|---|---|
| 2,424,199 | 7/1947 | Horst | 167/33 |
| 4,676,985 | 6/1987 | Gould et al. | 424/195.1 |
| 4,855,319 | 8/1989 | Mikolajezak et al. | 514/473 |
| 4,960,791 | 10/1990 | Klocke et al. | 514/468 |
| 5,047,242 | 9/1991 | Klocke et al. | 424/195.1 |
| 5,290,557 | 3/1994 | Mason et al. | 424/410 |

OTHER PUBLICATIONS

Haynes et al, C.A. #86:151443 (1977).
Ayyangar et al, C.A. #108:37735 (1988).
Nishikubo, C.A. #85:160104 (1976).

*Primary Examiner*—Allen J. Robinson
*Attorney, Agent, or Firm*—Litman, McMahon & Brown, L.L.C.

[57] ABSTRACT

Benzofuroxan, carboxybenzofuroxan and salts thereof have been identified as insect feeding deterrents with reduced or minimal toxicity relative to halogenated benzofuroxans which are utilized as insecticides. Preferred feeding deterrent compositions include an insect feeding deterrent effective amount of carboxybenzofuroxan or a salt thereof and a suitable carrier.

6 Claims, No Drawings

BENZOFUROXAN DERIVATIVES FOR USE AS INSECT FEEDING DETERRENTS

This application is a non-provisional application based on Provisional application Ser. No. 60/013,817 filed Mar. 21, 1996, and entitled INSECT FEEDING DETERRENTS AND THEIR SYNTHESIS.

BACKGROUND OF THE INVENTION

The present invention relates to the identification of compounds which deter feeding by insects and in particular the use of benzofuroxan and derivatives thereof as feeding deterrents.

Heavy use of insecticides presents environmental dangers and promotes the development of resistant insect populations. One alternative to present practices relating to insecticide use involves the application on crops of chemicals which inhibit or deter feeding thereon by insects with reduced or minimal toxicity to animals.

SUMMARY OF THE INVENTION

The present invention comprises the use benzofuroxan and mono-substituted benzofuroxans as feeding deterrents. The benzofuroxans identified for use as feeding deterrents generally include the following:

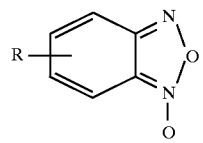

where R is H, OH, $CO_2H$ or $CO_2M$, where M is a Group I or II cation. For example, a preferred feeding deterrent composition comprises a feeding deterrent effective amount of 5-carboxybenzofuroxan and a suitable carrier.

OBJECTS AND ADVANTAGES OF THE INVENTION

The objects of the present invention include: providing feeding deterrent compositions which are relatively non-toxic and relatively inexpensive to manufacture and to apply at concentrations which are effective at deterring feeding by insects on plants and crop material; providing such compositions which are relatively easy to manufacture; providing such compositions which are effective at deterring feeding even at relatively low concentrations with respect to the plant or crop material to which the compositions are applied; and providing such compositions which are relatively biodegradable.

It is a further object of this invention to identify derivatives of benzofuroxan which function as feeding deterrents but are relatively non-toxic, non-irritating, soluble in water and relatively inexpensive to manufacture and to apply at concentrations which are effective at deterring feeding on plants and crop material.

Other objects and advantages of this invention will become apparent from the following description wherein are set forth, by way of illustration and example, certain embodiments of this invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific composition and functional details disclosed herein are not to be interpreted as limiting, but merely as a basis for the claims and as a representative basis for teaching one skilled in the art to variously employ the present invention in virtually any appropriately detailed structure.

The present invention comprises the use benzofuroxan and mono-substituted benzofuroxans as feeding deterrents. The benzofuroxans identified for use as feeding deterrents generally include the following:

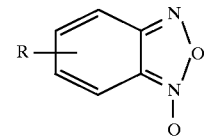

where R is H, OH, $CO_2H$ or $CO_2M$, where M is a Group I or II cation. For example, a preferred feeding deterrent composition comprises a feeding deterrent effective amount of 5-carboxybenzofuroxan or the sodium salt thereof and a suitable carrier.

Halogenated benzofuroxans have been reported as potent insecticides which are also highly toxic to humans and other animals. However, benzofuroxan has not been reported as an insect feeding deterrent and is only slightly toxic to humans. It has been postulated that an insect food sensory protein has amino and thiol groups with rigid steric requirements for binding via conjugate addition/redox reaction or imine/heterocycle formation with active compounds. It is postulated that benzofuroxan reacts with the insect food sensory protein to deter feeding generally as follows:

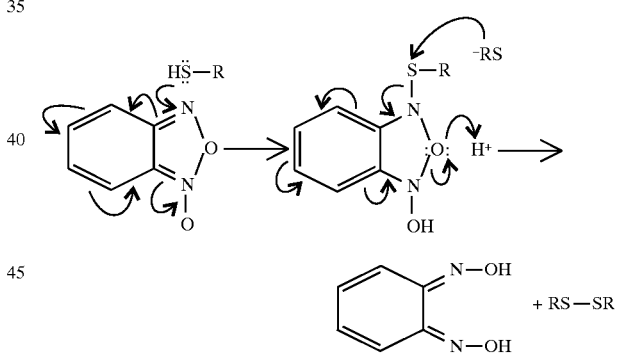

It is not exactly known how this reaction deters feeding. The reaction is believed to effect the insect nervous system and interfere with the insects ability to process information concerning food possibly suppressing hunger or decreasing the palatability of the treated food. The benzofuroxan may also arrest insect development beyond the larval stage.

Benzofuroxan is commercially available in large quantities and is relatively inexpensive. Benzofuroxan is a solid at ambient conditions at which it is to be applied for feeding deterrent effect and is also relatively insoluble in water.

It has also been discovered that certain mono-substituted benzofuroxans exhibit a feeding deterrent effect often with reduced or insignificant toxicity to animals. Preferred substituent groups include carboxylic acid and salts thereof with the Group I and II cations. The Group I cations include lithium, sodium, potassium, rubidium, cesium and francium. The Group II cations include beryllium, magnesium, calcium, strontium, barium and radium. Carboxybenzofuroxan is somewhat soluble in water at ambient conditions and the salts thereof are generally completely soluble in water at ambient conditions. Carboxybenzofuroxan and the salts thereof are generally solids at ambient conditions.

Methods of synthesizing carboxybenzofuroxan are well known in the art. Carboxybenzofuroxan was prepared by heating a mixture of lithium azide (2.88 g, 0.059 mol) and 4-chloro-3-nitrobenzoic acid (10.10 g, 0.50 mol) in 30 ml of hexamethylphosphorictriamide at 70–75 degrees Centigrade for 16 hours. The cooled reaction mixture was poured into one liter of water. The solid which formed was collected by suction filtration and dried at 20 degrees Centigrade and weighed 5.9 grams (66% yield of carboxybenzofuroxan). The product was purified by recrystallization from cyclohexane-toluene. It is believed that the carboxybenzofuroxan produced is 5-carboxybenzofuroxan. Salts of carboxybenzofuroxan can be prepared by well known means. For example, the sodium salt of carboxybenzofuroxan can be made by reacting carboxybenzofuroxan with a solution of sodium bicarbonate.

Although the carrier utilized in the tests discussed below comprises an organic solvent, ethyl acetate, it is not intended that the present application be limited to any particular carrier and it is foreseen that the active compounds of the present invention could be applied utilizing a wide range of carriers or formulations now known or subsequently developed. It is foreseen that the active compounds could be applied to crop or plant material in liquid or solid compositions or in solid suspensions or without a carrier. The benzofuroxan with a carboxyl salt substituent group is more readily soluble in water which is a preferred liquid carrier. It is also foreseen that a wide range of additives could also be utilized in the feeding deterrent compositions to facilitate application, to stabilize the composition and for other reasons well known in the art.

The feeding deterrent effect of various benzofuroxans was evaluated through choice tests and weight gain tests on third to fifth instar larvae of *Tenebrio molitor* (mealworm, flour beetle larvae), third-instar larvae of *Manduca sexta* (tomato hornworm) and with juvenile *Acheta domestica* (common cricket). Screening for toxicity was done with larvae of *Artemia salina* (brine shrimp). Insect cultures and food were obtained from Carolina Biological Supply Co., Burlington, N.C.

Test compounds in an ethyl acetate solution were applied by pipet to a weighed food sample and the mixture was stirred thoroughly in glass or stainless steel trays. References to concentrations of test compounds are reported as parts per million (ppm) by weight of pure test compound relative to the weight of the food sample. Treated food was left in open trays for twenty-four hours before insects were introduced. Controls of food treated with ethyl acetate were prepared according to the same procedure. Insect trials with food treated by solvent only (control) versus food with no treatment showed no evidence of solvent residue effects.

For the choice tests, forty *T. molitor* larvae were placed on a tray having a first and a second supply of bran meal (60 grams each) on opposite ends thereof. The larvae were placed in groups on each food supply. The first supply of bran meal was treated with a solution of the test compound and the carrier, ethyl acetate as noted above. The test compound was applied to the food at a selected concentration (generally 400 or 800 parts per million, i.e. weight of test compound to weight of bran meal). The second supply of bran meal was treated with an equivalent amount of ethyl acetate as noted above. The second supply of food may be referred to as untreated food. The first and second supplies of bran meal were maintained in separate areas in the container separated by a screen across which the larvae could traverse. The trays were covered with lids that allowed air flow.

The number of larvae at each end were counted at 7-day intervals. The percentage of larvae on the control or untreated food is indicative of the feeding deterrent effect of the test compound.

Growth tests of *T. molitor* were done by putting 40 larvae on 120 grams of treated and untreated food and periodically weighing the insects. Weight gain for insects on treated food is reported as a percentage of the weight gain for insects on the control or untreated food (i.e. weight gain on treated/ weight gain on control). The percentage of dead insects was also recorded. Typical mortality for the controls were 0% at 7 days, 3% at 14 days and 5% at 21 days.

Feeding tests with *M. sexta* were made by putting one insect in a covered dish containing two 3.5 cm culture dishes. The food was prepared according to the formula of Yamamoto reported in Yamamoto, R. T., *J. Econ. Entom.* 1969, 62, 1427. One dish contained 5.0 grams of food treated with the test compound and solvent and the other contained 5.0 grams of food treated with solvent only. Each dish was weighed at 1-day intervals for one week.

Feeding tests were also conducted with azadirachtin, the principle active component of neem oil, a natural product with well-documented insect feeding deterrence. Azadirachtin was obtained from Sigma Chemical Co., St. Louis, Mo. Results of feeding tests are shown in Table 2.

Table 1 provides results from the choice tests with *T. molitor*. The table includes an indication of the percentage of insect larvae in the area of the untreated food (i.e. the percentage which preferred the untreated food). The reference to days with each percentage indicates the number of days from the beginning of the test on which the observation was made.

TABLE 1

Choice Tests for Benzofuroxans

| Test Compound | Insect | Conc. (ppm) | % Insects on untreated food (7 days) | (14 days) |
|---|---|---|---|---|
| benzofuroxan | T. molitor | 800 | 80 | 53 |
| benzofuroxan | T. molitor | 400 | 75 | 78 |
| carboxybenzofuroxan | T. molitor | 800 | 75 | 60 |

TABLE 2

Weight Change Relative to Control

| Test Compound | Insect | Conc. (ppm) | % Wt change v. control (7 days) | (14 days) |
|---|---|---|---|---|
| benzofuroxan | T. molitor | 800 | 36 | 34 |
| benzofuroxan | T. molitor | 400 | 90 | 100 |
| carboxybenzofuroxan | T. molitor | 800 | 30 | 35 |
| sodium salt of CBFN* | T. molitor | 800 | 30 | 34 |

*CBFN is short hand for carboxybenzofuroxan

TABLE 3

Feeding Rate Relative to Control

| Test Compound | Insect | Conc. (ppm) | % Wt change v. control (7 days) |
|---|---|---|---|
| benzofuroxan | M. sexta | 400 | 59 |
| azadirachtin | M. sexta | 50 | 100 |

TABLE 4

Mortality Relative to Control

| | | Conc. | % Mortality v. control | |
|---|---|---|---|---|
| Test Compound | Insect | (ppm) | (7 days) | (14 days) |
| benzofuroxan | T. molitor | 800 | 25 | 35 |
| benzofuroxan | T. molitor | 400 | 0 | 10 |
| carboxybenzofuroxan | T. molitor | 800 | 5 | 30 |
| sodium salt of CBFN* | T. molitor | 800 | 3 | 10 |

*CBFN is short hand for carboxybenzofuroxan

For toxicity screening, a suspension of the test compound was prepared by sonicating a mixture of 40 mg of test compound and 250 ml of artificial sea water. One hundred *A. salina* larvae (brine shrimp) were introduced in the aerated mixture and the number of dead organisms was counted periodically. A control of artificial seawater alone was also utilized. Table 3, provides results from toxicity screening of selected compounds.

TABLE 5

Toxicity Screening

| | Number Dead/100 | |
|---|---|---|
| Compound | 4 days | 7 days |
| benzofuroxan | 100 | 100 |
| carboxybenzofuroxan | 12 | 28 |
| control | 6 | 31 |

Although benzofuroxan showed relatively high toxicity to brine shrimp, brine shrimp are relatively sensitive and the associated toxicity to animals may be relatively small and further research as to the toxicity is necessary. The carboxybenzofuroxan showed relatively low toxicity particularly in view of the sensitivity of brine shrimp.

Although the active compounds disclosed herein are discussed for use in deterring insects from feeding of plant and crop material and the like it is foreseen that the active compounds may also exhibit a feeding deterrent effect on terrestrial mollusks, nematodes or other related creatures which feed on plant and crop material.

Further it is foreseen that various chemical equivalents or isomers of the specified active compounds may also provide a feeding deterrent effect.

It is to be understood that while certain forms of the present invention have been illustrated and described herein, it is not to be limited to the specific forms or compositions, equivalents or isomers described and shown.

What is claimed and desired to be secured by Letters Patent is as follows:

1. A method of deterring the feeding activity of insects on plant and crop material comprising the step of (a) applying to said material with a feeding deterrent effective amount of an active compound of the formula:

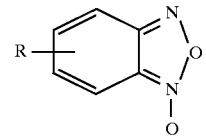

where $R_1$ is H, $CO_2H$ or $CO_2M$ where M is a Group I or Group II cation.

2. The method as in claim 1 wherein:

(a) said active compound comprises benzofuroxan.

3. The method as in claim 1 wherein:

(a) said active compound comprises carboxybenzofuroxan.

4. The method as in claim 1 wherein:

(a) said active compound comprises 5-carboxybenzofuroxan.

5. The method as in claim 1 wherein:

(a) said active compound comprises a sodium salt of carboxybenzofuroxan.

6. The method as in claim 1 wherein: (a) said active compound comprises a sodium salt of 5-carboxybenzofuroxan.

* * * * *